United States Patent [19]

Korth

[11] Patent Number: 5,530,023
[45] Date of Patent: Jun. 25, 1996

[54] PRODUCTION OF BINDING SITES FOR PAF, PAF ANALOGUES AND PAF ANTAGONISTS IN ENDOTHELIAL CELLS

[76] Inventor: Ruth Korth, Palestrinastr.9, D-806390 München, Germany

[21] Appl. No.: 172,234

[22] Filed: Dec. 23, 1993

Related U.S. Application Data

[63] Continuation-in-part of Ser. No. 845,088, Mar. 3, 1992, Pat. No. 5,356,791, Ser. No. 104,599, Aug. 11, 1993, Pat. No. 5,480,881, and Ser. No. 994,752, Dec. 22, 1992, abandoned, which is a continuation-in-part of Ser. No. 259,674, Oct. 19, 1988, abandoned, said Ser. No. 104,599, is a continuation of Ser. No. 844,882, Mar. 3, 1992, abandoned, which is a continuation-in-part of Ser. No. 704,554, May 23, 1991, abandoned.

[30] Foreign Application Priority Data

Dec. 28, 1992 [DE] Germany .................. 42 44 265.6

[51] Int. Cl.⁶ .................................................. A61K 31/34
[52] U.S. Cl. ............................................................ 514/468
[58] Field of Search ............................................... 514/468

[56] References Cited

U.S. PATENT DOCUMENTS

| 4,571,407 | 2/1986 | Chatterjee et al. ............ 514/454 |
| 4,734,280 | 3/1988 | Braquet ........................ 424/195.1 |
| 4,900,729 | 2/1990 | Stransky et al. ................ 514/220 |

FOREIGN PATENT DOCUMENTS

| 23943/88 | 8/1991 | Australia . |
| 0256687A1 | 2/1988 | European Pat. Off. . |
| 0312913B1 | 10/1988 | European Pat. Off. . |
| 0459432A1 | 12/1991 | European Pat. Off. . |
| 0540767A1 | 5/1993 | European Pat. Off. . |

OTHER PUBLICATIONS

D. Steinberg, S. Parthasarathy, T.E. Carew, J. C. Khoo and J. L. Witztum (1989) New Engl. J. Med. 320, 915–914.
J. Benveniste et al., (1972) J. Exp. Med. 13, 1356–1377.
J. Benveniste et al., C. R. Acad. Sci. (Paris) 289, 1037–1040. (1979).
C. A. Demopoulos et al., (1979) J. Biol. Chem. 254, 9355–9358.
R. Korth et al., (1983) Chem. Phus. Lipids 33, 47–53.
R. Korth et al., (1988) Eur. J. PHarmacol. 152, 101–110.
R. Korth et al., (1989) Brit. J. Pharmacol. 98, 653–661.
Z. I. Honda et al., (1991) Nature 349, 342–346.
FEBS Lett. 226 (1988), 371–376.
R. Korth and J. Benveniste (1987) Eur. J. Pharmacol. 142, 331–334.
Br. J. Pharmacol. 90, pp. 139 (1987).
J. Exp. Pharmacol. Exp. Therapeutics 257, 1991, pp. 374–381.
R. Korth U.S. Trademark Application, Ser. No. 74/416,579, date of filing Jul. 26, 1993.
Goldman et al., New Engl. J. Med. 318, pp. 397–403, 1990.
Int. J. Cancer 17 (1976), 556–577.
American Type Culture Collection (ATCC 6th Ed. CRL 1593) p. 154 (1987).

*Primary Examiner*—Kimberly Jordan
*Attorney, Agent, or Firm*—Nikaido, Marmelstein, Murray & Oram

[57] ABSTRACT

The invention refers to the production of substances which prevent and treat disorders caused by pathological cell differentiation leading to enhanced LA-paf effect and production. The invention refers to simple methods to test and produce LA-paf antagonists and paf antagonists against very high affinity paf receptors on endothelial cells. According to the invention genes producing endothelial paf receptors in endothelial cells during differentiation for example in response to insulin can be transferred from adherent endothelial cell lines to soluble cells. Endothelial cell lines for example immortalized endothelial cells can also be cultured on soluble particles for screening procedures. Substances which prevent and inhibit very high affinity paf receptors and LA-paf production antagonize pathological differentiation, irritation, aging and death of cells. The antagonists can be administered for example with food.

7 Claims, 2 Drawing Sheets

PRODUCTION OF BINDING SITES FOR PAF, PAF ANALOGUES AND PAF ANTAGONISTS IN ENDOTHELIAL CELLS

This application is a continuation-in-part of U.S. patent application Ser. No. 07/845,088, filed Mar. 3, 1992, now U.S. Pat. No. 5,356,791. This application is a continuation-in-part of U.S. patent application Ser. No. 08/104,599, filed Aug. 11, 1993, now U.S. Pat. No. 5,480,881, which is a continuation of Ser. No. 07/844,882, filed Mar. 3, 1992, which is a continuation-in-part of U.S. patent application Ser. No. 07/704,554 filed May 23, 1991, now abandoned. This application is also a continuation-in-part of U.S. patent application Ser. No. 07/994,752, filed Dec. 22, 1992, now abandoned, which is a continuation-in-part of U.S. patent application Ser. No. 07/259,674 filed Oct. 19, 1988, now abandoned.

The invention refers to the use of LA-paf antagonists and a procedure for determining the efficacy of antagonists against LA-paf. According to the invention endothelial cells produce very high affinity paf receptors after their differentiation. Specific antagonists against very high affinity paf receptors for example on endothelial cells should be found by screening procedure. According to the invention, very high affinity paf receptors, preferably on endothelial cells, are correlated with LA-paf production. FIG. 2 shows that the uptake of paf and its metabolism to LA-paf depend upon very high affinity receptors on endothelial cells (as unlabelled paf was inhibitory). Thus, LA-paf antagonists and antagonists against very high affinity paf receptors can be used to treat or prevent pathological differentiation, irritation, aging or death of endothelial cells. Antagonists can be administered for example with food or beauty products to individuals requiring the said substances. The invention refers to simple procedures to test antagonists against LA-paf effects and production. A transfer of corresponding genes which encodes the production of very high affinity paf receptors from differentiated endothelial cells for example to soluble cells is suitable to conduct quick and simple screening procedures, preferably by automated machines.

Beside allergic and inflammatory disorders phospholipids may play an initiating role in vascular disorders for example artherosclerosis [for review D. Steinberg, S. Parthasarathy, T. E. Carew, J. C. Khoo and J. L. Witztum (1989) New Engl. J. Med. 320, 915–924]. Ether phospholipids require for their biological activity at least an ether group in sn-1 position of the glycerol with a short acyl chain in position 2. Paf-acether (paf, originally platelet activating factor) [J. Benveniste et al. (1972) J. Exp. Med. 13, 1356–1377] is a potent inflammatory mediator, chemically 1-0-alkyl-2-acetyl-sn-glycero-3-phosphocholine with an acetyl group in position 2 and saturated or non-saturated alkyl-groups in position 1 of the molecule [[J. Benveniste et al. C. R. Acad. Sci. (Paris) 289, 1037–1040, C. A. Demopoulos et al. (1979) J. Biol. Chem. 254, 9355–9358, R. Korth et al. (1983) Chem. Phys. Lipids 33, 47–53]. Only ether phospholipids esterified in position 2 with maximal 4 carbon fatty acid derivates such as 1-0-alkyl-2-butyroyl-sn-glycero-3-phosphocholine exhibit similar biological potency as compared with paf. In contrast, oxidized compounds with an ester group in position 1 of the molecule are more than 1000 fold less potent as compared with paf [C. A. Demopoulos et al. (1979) J. Biol. Chem. 254, 9355–9358].

According to the invention paf plays an important role in vascular diseases. In addition, paf seems to be involved in the development of atherosclerotic lesions. This theory is based on the following findings: 1) Cells involved in atherosclerosis such as monocyte/macrophage like cells synthesize paf in response to various stimuli; 2) the atherogenetic low density lipoprotein (LDL) and cholesterol cause expression of specific paf binding sites on monocyte/macrophage like cells mediating monocyte emigration from inside the vessels out [R. Korth, Eur. Patent (20/10/87), Publ. Nr. 0312 913 B1; Germany P4017818.8 (Jun. 1, 1990) and P4034090.2 (Oct. 26, 1990)].

The present invention refers to a quick and simple methods to test the efficacy of paf antagonists with differentiated vs. non-differentiated endothelial cells. Non-differentiated endothelial cells are, for example, immortalized endothelial cell lines, preferably immortalized umbilical vein endothelial cells (Im-Huvec). This invention also refers to methods of endothelium differentiation with various factors, for example with growth factors, preferably insulin. According to the invention, endothelial cells produce very high affinity paf receptors during differentiation as compared with the absence of paf receptors on non-differentiated endothelial cells, for example on non-differentiated Im-Huvec. According to the invention very high affinity paf receptors interfere with cellular production of LA-paf and antagonist inhibit both LA-paf effects and production. Paf uptake is receptor dependent as unlabelled ligand paf was inhibitory. FIG. 2 showed LA-paf production during cellular paf metabolism. Indeed, specific paf receptor antagonists inhibit as well the effect of LA-paf as the synthesis of LA-paf. LA-paf is produced from paf, preferably exogenously added paf, as shown in FIG. 2.

According to the invention, genes encoding very high affinity paf receptors in endothelial cells should be produced by differentiation and enriched, for example, by culture of immortalized endothelial cells. Next, transfer of genes to soluble cells or bacterial cells are performed according to standard procedures for example injection or electrical methods as described in Honda et al., Nature 349, pp. 342–346, 1991.

The invention refers to a procedure to test very high affinity paf receptors on soluble cells or endothelial cells cultured on soluble particles.

Specific paf receptor antagonists such as triazolothienodiazepines share similar pharmacological properties with chemically defined extracts of natural Ginkgo biloba, a plant used in the traditional Chinese medicine as treatment against lung and heart diseases. For example various triazolothienodiazepines are known to interact with high affinity (ha) paf receptors on human platelets as the antagonist $IC_{50}$ values correlated closely for paf binding and paf-mediated platelet aggregation (or $Ca^{2+}$ flux) and a parallel rightward shift of the paf dose response curve reaches maximal values with inefficiency of WEB 2086 against platelet aggregation in response to aspirin and ADP [R. Korth et al. (1988) Eur. J. Pharmacol. 152, 101–110; R. Korth et al. (1989) Brit. J. Pharmacol. 98, 653–661]. High affinity paf receptors and paf metabolism in cancer cell lines have been reported [R. Korth, European Patent Application (1990) Bulletin 91/49, Publication Number 0 459 432 A1]. High affinity paf receptors from guinea pig lungs and blood cells have been demonstrated on the molecular level [Z. I. Honda et al. (1991) Nature 349, 342–346]. In contrast, LA-paf antagonists for example antagonists against very high affinity paf receptors by preference on endothelial cells related with LA-paf production are not defined up to now.

LA-paf is physicochemically and functionally distinct as compared with chemically defined paf [R. Korth, European Patent Application (1990) Bulletin 91/49, Publication Number 0 459 432 A1]. The invention refers to in vitro production of LA-paf by soluble cells to facilitate the use of purified labelled and unlabelled LA-paf as ligand for binding studies. Cellular LA-paf production is a quick and simple method to produced large quantities of labelled LA-paf in vitro.

Whereas LA-paf is a preformed mediator present in healthy persons, cellular paf is not normally present at detectable levels. In contrast to cellular paf, plasma paf has been found in human plasma (peak x) because it has been chemically defined as a compound which comigrates with paf after purification using high pressure liquid chromatography [FEBS Lett. 226 (1988), 371–376]. Fatty acid free serum albumin is a paf carrier and it inhibits platelet activation and paf binding in a non-specific manner [R. Korth and J. Benveniste (1987) Eur. J. Pharmacol. 142, 331–341].

The substance that antagonize LA-paf can be a triazolothieno-diazepine or analogous as well as homologous compounds. In addition ginkgolides and paf analogues, such as CV 3988, are suitable. Triazolothieno-diazepines are described in Br. J. Pharmacol. 90, pp 139 (1987), ginkgolides in Eur. J. Pharmacol. 152, pp 101–110 (1988). Of the triazolothieno-diazepine compounds WEB 2086 and WEB 2098 are especially suitable. Of the ginkgolides BN 52020, BN 52021 and a mixture of BN 52020, BN 52021 and BN 52022, which is referred to as BN 52063, achieve the best results [R. Korth et al. (1988) Eur. J. Pharmacol. 152, 101–110]. The synthetic compound BN 50739 [J. Exp. Pharmacol. Exp. Therapeutics 257, 1991, pp. 374–381] can also be used.

The chemical term of CV 3988 is rac-3-(N-n-octadecyl carbamoyl oxy)-2-methoxypropyl 2-tiazolioethyl phosphate; the term of WEB 2086 is 3-(4-(2-chlorophenyl)-9-methyl-6H-thieno(3,2-f) (1,2,4) triazolo-(4,3-a)-(1,4)diazepine-2yl)-1-(4-morpholinyl)-1-propanone; the term of WEB 2098 is (3-(4-(2-chlorophenyl)-9-cyclopropyl-6H-thieno (3,2-f)-(1,2,4) triazolo-(4,3-a) (1,4) diazepine-2yl)-1-(4-morpholinyl)-1-propanone; the term of BN 52020 is 9H-1, 7a- Epoxymethano)-1H, 6aH-cyclopenta(c)furo(2,3-b) furo(3',2':3,4) cyclopenta (1,2-d) furan-5,9,12 (4H)-trione, 3 -tert-butylhexahydro-4, 7b-dihydroxy-8-methyl; the term of BN 52021 is 9H-1, 7a-Epoxymethano)-1H,6aH-cyclopenta(c)furo(2,3-b)furo-(3',2':3,4) cyclopenta(1,2-d) furan-5,9,12(4H)- trione, 3 tert-butylhexahydro-4, 4b-11-trihydroxy-8-methyl; and the term of BN 52022 is 9H-1, 7a-(Epoxymethano)-1H, 6aH-cyclo-penta(c)furo(3',2':3,4) cyclopenta (1,2-d) furan-5,9,12 (4H)-trione, 3 tert-butyl hexahydro-2,4,7b,11-tetrahydroxy-8-methyl. The chemical term of BN 50739 is tetrahydro-4,7,8,10 methyl (chloro-2 phenyl)6 (dimethoxy-3,4-phenyl) thio) methylthiocarbonyl-9 pyrido (4',3'-4, 5) thieno (3,2-f) triazolo-1,2,4 (4, 3-a) diazepine-1,4).

The paf antagonist can be administered topically, orally, parenterally, by liposomes, food, beauty products, syrups or inhalation. According to the invention paf or LA-paf antagonists can also be administered in form of food for example with "FIDA infants' foods for invalids and seniors" [R. Korth U.S. Trademark application, Ser. No. 74/416579, date of filing Jul. 26, 1993]. The compounds are administered as active ingredients in conventional pharmaceutical preparations, e.g. in compositions comprising an inert pharmaceutical vehicle and an effective dose of the active substance, such as tablets, coated tablets, capsules, lozenges, powders, solutions, suspensions, aerosols for inhalation, ointments, emulsions, syrups, food, suppositories, etc. The effective dose range of the compounds according to the invention includes at least 0.1 to 500, preferably between 0.1 and 50, mg per dose for intravenous or intramuscular application.

Medicaments containing bilobalid can be used to control nervous diseases as described (U.S. Pat. No. 4,571,407, 1986). According to the invention natural Ginkgo biloba is administered by food for example "FIDA infants' foods for invalids and seniors" to prevent and treat irritation pathological differentiation, aging and death of cells. The administration with food by preference of ginkgolides is suitable for example for older persons and children. The invention is suitable to compose "FIDA infants' foods for invalids and seniors" to prevent disorders caused by differentiation, degeneration, genetic disorders, irritation, aging and death of cells.

Water intoxication has been shown to be a serious problem in many patients with chronic disorders (Goldman et al., New Engl. J. Med. 318, pp. 397–403, 1990). For example, psychiatric patients have polydipsia and hyponatremia with unexplained defects in urinary dilution, osmoregulation of water intake and secretion of vasopressin. LA-paf antagonist can be administered to prevent and antagonize episodic defects in osmoregulation of water intake with diverse neurological and mental symptoms.

The "treatment of paf-acether-induced maladies" with ginkgolides has been described before in U.S. Pat. No. 4,734,280, (1988). Similarly, U.S. Pat. No. 4,900,729, (Feb. 13, 1990), by Stransky et al. concerning thieno-1,4-diazepines treated disorders caused by chemically defined platelet activating factor. In contrast, LA-paf has been shown to be physicochemically and functionally distinct from paf (paf-acether) [R. Korth, European Patent Application (1990) Bulletin 91/49, Publication Number 0 459 432 A1], with LA-paf present in cells of healthy persons. U.S. patent application Ser. No. 07/704,554, Table 1, discloses the functional differences between paf and LA-paf; unlabelled paf significantly decreased, whereas LA-paf or LDL significantly increased, labelled paf binding. Also shown in FIG. 1, the physicochemical difference of paf and LA-paf using high pressure liquid chromatography as LA-paf eluted with a retention time of 9–11 minutes from standard phase as compared with 19–23 minutes retention time of paf. Other patents refer also to chemically defined paf and/or antagonists non-related to triazolothieno-diazepines with "the excellent platelet activating factor antagonism" of "thiazolidin-4-one derivatives and acid addition salts thereof" [Eur. Patent Appl. Nr. 87306508.0 (1988)]. All references are silent concerning LA-paf antagonists.

According to the invention the antagonists are specifically suitable to treat pathological water osmoregulation with irritation of brain and prevent cells of cell irritation, aging, degeneration, and death. They antagonize growing old before age by protection of the subendothelial tissue. Antagonists with an effect on the central nervous system have to penetrate the endothelial blood brain barrier to protect neuronal cells. LA-paf antagonists defined herewith protect the endothelial barrier via interaction with very high affinity paf binding sites. Recently we showed a new neurotransmitter lyso paf interacting with specific lyso paf receptors [R. Korth, Eur. Appln. No. 91118745.8, 1991]. Lyso paf with the chemical structure 1-0-alkyl-sn-glycero-3-phosphocholine is a deacetylated precursor and metabolite of paf which does not activate platelets or endothelial cells but it modulates the endothelium by intermediate of activated leukocytes.

According to the invention endothelial cells for example immortalized endothelial cells after differentiation are used to test the efficacy and specificity of antagonists. In order to conduct a quick and simple test on the efficacy with regard to their antagonistic activity vis-a-vis paf receptors, i.e. to use a screening procedure, for example, to find effective antagonists to paf receptors which can then be taken into consideration for treating or preventing disorders caused by pathological irritation, differentiation, aging or death of cells, then according to the invention, the best method is to proceed as follows.

a) Non-differentiated endothelial cells are mixed with at least one compound of various differentiation factors for example lipoproteins, lipoprotein-associated paf, steroids such as cholesterol, growth factors such as insulin, hormones such as erythropoietin etc., cytokines, PMA, DMSO and acid medium, b) a given quantity of purified cells is mixed with a given quantity of labelled paf or LA-paf and the antagonist to be determined, c) a given quantity of the same purified cells is mixed with a given quantity of labelled paf or LA-paf in the absence of antagonists, d) the cells are separated from the mixtures b) and c) in each case, e) the quantity of labelled paf or LA-paf bound to the cells is measured in each case, and f) the efficacy of the paf or LA-paf antagonist is determined from the relationship between the quantity of labelled paf or LA-paf which is bound to the cells according to b) in the presence of the antagonist on one hand, and the quantity of labelled paf or LA-paf which is bound to the cells according to c) in the absence of the antagonist on the other hand.

Preferably human umbilical vein endothelial cells (Huvec) or non-differentiated endothelial cells for example immortalized cells (Im-Huvec) after differentiation are used for the procedure. The invention determines the efficacy of LA-paf antagonists or antagonists specifically directed against endothelial paf receptors.

Differentiation for example of Im-Huvec can be performed by non-specific cell stimulation. Thus, cells can be differentiated for example with LDL, LA-paf or insulin or by activation of the protein kinase C for example by PMA.

It is known that the cells are preferably separated from the buffer by centrifugation or filtration. As labelled ligands also labelled agonists and antagonists or antibodies can be used as well as labelled or unlabelled colored or fluorescence labelled paf or LA-paf or analogues. Endothelial cells are preferably washed with acid buffer and detached after the binding procedure in a cool medium with EDTA and without Magnesium and Calcium.

In case that endothelial cells are used, the procedure of the present invention can be used to determine the activity of highly specific paf antagonists. Endothelial cells produce very high affinity paf receptors during differentiation as compared with tenfold distinct high affinity paf receptors on blood cells and cancer cells. Thus, endothelial cells and blood cells produce distinct paf receptors on their surface. Non-differentiated (immortalized) endothelial cells for example immortalized endothelial cells have no paf receptors but produce them during their differentiation.

According to the invention, specific paf antagonists against very high affinity paf receptors can be used for the prophylaxis and treatment of pathological irritation, differentiation, aging and death of cells for example in cases of risk factors such as hyperlipidemia, hyperinsulinemia and acid pH values. Chronical cell irritation with activation of the protein kinase C interferes for example with cancer disease and metastasis. Pathological differentiation of endothelial cells for example in response to insulin, cholesterol, lipoproteins (normal or modified) or acid blood pH values has a considerable importance in inflammatory, allergic, vascular, chronical and genetic diseases.

Preferably endothelial cells cultured on dishes or on soluble particles such as methylcellulose or latex beads, but also soluble cells, by preference after gene transfer for example cancer cells or bacterial cells, are used for the procedure of the invention determining the efficacy of distinct LA-paf antagonists.

The mixing according to the steps b) and c) is done preferably at a temperature of 20° C. After mixing, the cells are incubated preferably 30 min. Before they are separated according to step d) of the procedure of the present invention. The separation of the cells according to step d) can be performed by filtration or centrifugation. After this, the quantity of labelled paf or LA-paf which is (specifically) bound to the cells is determined. If radioactively labelled paf or LA-paf is used, only the radioactivity bound to cells is measured. The radioactivity bound in the filter without cells is subtracted from these values. By drawing calibration graphs, which are obtained with varying quantities of the antagonist in accordance with step b), it is thus possible to obtain the efficacy of the antagonist at a 50% inhibitory value, i.e. as that quantity of the antagonist which, in relation to a given quantity of cells, leads to a 50% inhibition of the reversible paf binding. It is also possible to calculate binding kinetics of antagonists.

Antibodies by preference monoclonal antibodies against LA-paf itself or paf receptors can be formed for diagnostic tests. The invention refers to produce LA-paf in large amounts an essential condition for production of antibodies or of enzyme assays. Diagnostic tests for the clinical use can be facilitated using special testing containers which are commercial available and which are modified for smaller blood volumes as proposed in German utility model application G 87 16 004.8.

Since the specific binding of paf or paf-like compounds such as LA-paf (but not lyso paf) is in close correlation with the cellular calcium stream, the procedure of the present invention can also be used for measuring paf, LA-paf and agonists for example by comparing their effects on the cellular calcium stream with calibration graphs of synthetic paf or mediator production and release.

BRIEF DESCRIPTION OF THE DRAWINGS

FIG. 1A Scatchard plot analysis of specific [$^3$H] paf binding. Values are means of three experiments shown in FIG. 1B.

Figure 1A:
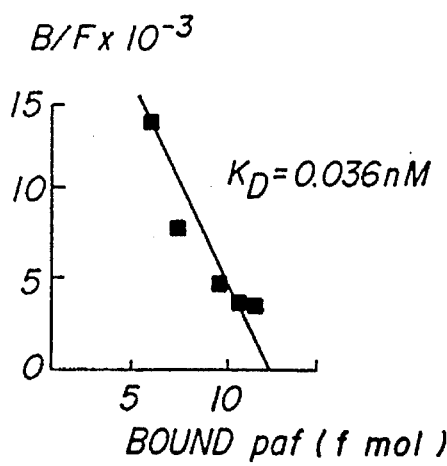
FIG. 1A

[$^3$H]paf binding to differentiated Im-Huvec (20° C., 30 min, 0.25% BSA). The total [$^3$H]paf binding (●) and the non-specific [$^3$H]paf binding (o) were determined in the absence or presence of 50 nM unlabelled paf to yield the saturated specific [$^3$H]paf binding (■).

Values are in pM bound [$^3$H]paf to one confluent dish of Im-Huvec. They are means ±1 s.d. of three distinct experiments.

FIG. 2A

Endothelial cells and their supernatants were extracted separately to perform HPLC using standard procedure. Paf (●o) and LA-paf (■□) in endothelial cells were calculated in fmol as means of duplicates and are representative of two experiments.

Concentration-dependent [$^3$H]paf metabolism by endothelial cells and their supernatants. Endothelial cells were incubated with increasing concentrations of [³H]paf as defined in the absence (●■▲) or presence (o□△) of unlabelled paf (500 nM) (30 min, 20° C., 0.25% BSA).

EXAMPLE 1. SPECIFIC ANTAGONISTS

1.1. Culture of endothelial cells

Endothelial cells for example immortalized umbilical endothelial cells (Im-Huvec) were cultured by preference in a M199 medium containing 25 mM Hepes and 2 g/l NaHCO₃, 10% heat-inactivated foetal calf serum, 1% amino acids, 1% folic acid, 1% RPMI vitamines, 0.1% gentamycin and 4 mM glutamine (Gibco, Paisley, Scotland). The cells were incubated in 75 cm² culture flask on 0.2% gelatine with media changes every 2–3 days. When cultures reached confluence (3–5 days), the cells were harvested by brief exposure to trypsin-EDTA and plated into culture dishes coated with 0.2 % gelatin at 1:3 split ratio. Endothelial cells were grown thereafter by preference 5 days to be cultured then for example with or without addition of human insulin (2 I.U. per 5 ml medium) for 20 hr incubation period before washing. Cells at passage eleven were used throughout this study, and were characterized as endothelial cells using a standard procedure [Eur. P 3735525.2 from 20/10/87].

1.2. Binding studies with [³H]paf

For example immortalized endothelial cells (Im-Huvec) were tested because the number of endothelial cells prepared freshly from one umbilical vein cord was limited. Im-Huvec were incubated with [³H]paf (100–600 pM, 0.25% BSA, 30 min at 20° C.)) and specific [³H]paf binding was assessed in the absence vs presence of 50 nM paf. Im-Huvec were cultured before 20 hr in a medium with or without addition of human insulin (2 I.U. per 5 ml, Hoechst, Germany). After the binding procedure free radioactivity was washed twice from the confluent monolayer with Tyrode's buffer (pH 6.4) containing BSA and then once with cold isotonic NaCl-EDTA (5 mM) solution. Cells were detached by incubation in the latter medium keeping the dishes on ice for at least 30 min. Detached cells were separated from the medium by vacuum filtration onto GF/C filters in a Millipore vacuum system. Incubation and washing buffers as well as control buffers were filtered to recover cells detached during the washing procedures. Filters were washed twice with cold Tyrode's buffer and the radioactivity of the filter-bound endothelial cells was counted under standard conditions in scintillation fluid. Filter-bound radioactivity without endothelial cells was subtracted from filter-bound radioactivity with endothelial cells. [³H]paf bound to confluent endothelial cells in one dish was expressed either in fmol/ml or in pM.

1.3. Binding of [³H]paf to Im-Huvec

We investigated endothelial cells as described [Eur. P 3735525.2 from 20/10/87]. This invention refers to non-differentiated cells for example Im-Huvec after differentiation with production of very high affinity paf receptors. According to the invention Im-Huvec were cultured for example 20 hr in the presence of insulin. Paf binding studies were performed to calculate the binding kinetics of endothelial receptors with Scatchard plot analysis. Indeed, specific and saturated [³H]paf binding to differentiated Im-Huvec reached very high affinity $K_D$- values of 0.036 nM. In these experiments unlabelled paf was used as unlabelled ligand (0.25%, 20° C., 30 min, FIG. 1). In contrast, no specific [³H]paf binding was detected when Im-Huvec were cultured without addition of human insulin (not shown, n=3).

According to the invention differentiated, but not non-differentiated, Im-Huvec produced paf receptors. According to the invention for example the presence of 2 I.E. human insulin for 20 hr incubation period produced very high affinity paf receptors. The adherent confluent endothelial cells bound without insulin only 6.8 fmol radiolabelled paf. In contrast endothelial cells bound 68 fmol radiolabelled paf per culture dish of adherent confluent endothelial cells after differentiation by preference with long time culture (20 hr) in the presence of 2 I.E. human insulin. Total [³H]paf binding to non-differentiated cells was not inhibited in the presence of unlabelled paf (50, 500 nM) excluding paf receptors. In contrast, unlabelled paf decreased paf binding to differentiated Im-Huvec. The total binding decreased from 68 fmol to 53.7 fmol and to 28.1 fmol in the presence of 50 and 500 nM unlabelled paf. Thus, insulin produced very high affinity paf receptors as compared with no paf receptors on resident Im-Huvec. In other words Im-Huvec produced only paf receptors after differentiation for example with growth factor such as insulin whereas no paf receptors are present on the surface of resident Im-Huvec according to the invention.

An antagonist for example BN 50739 (10 and 20 µM) do not modulate paf binding to resident Im-Huvec. However, according to the invention the antagonist BN 50739 (20 µM) reached specific paf binding of 5.8 fmol per culture dish of adherent confluent endothelial cells when Im-Huvec were differentiated for example in the presence of insulin. According to the invention non-differentiated endothelial cells produce very high affinity paf receptors after their differentiation. The tested substance is suitable to antagonize paf receptors on differentiated endothelial cells. According to the invention this antagonist is suitable to prevent and treat pathological cell differentiation and to protect the (sub)endothelium tissue for example against paf and LA-paf.

In order to perform a simple procedure to test antagonists preferably against very high affinity paf receptors on endothelial cells genes can be enriched, defined and transferred for example into soluble cells by preference of cell lines and bacterial cells. The invention refers to transfer by preference genes producing very high affinity paf receptors and interfering with LA-paf production to soluble cells for screening procedures performed for example by automatons. It is suitable to use soluble cells instead of adherent cells to facilitate screening procedures of new compounds directed for example specifically against very high affinity paf receptors. Alternatively endothelial cells can be cultured on soluble particles. The latter possibility is also suitable because post receptor events specifically related to endothelial cells define also the structure of the receptor protein. The same gene might produce paf receptors with different cell-specific structures for example via distinct phosphorylation and/or distinct receptor modulating G-proteins etc. The antagonists can be tested according to the following procedure:

a) Endothelial cells are cultured, b) endothelial cells are mixed with at least one differentiation factor producing paf receptors for example the growth factor insulin, c) endothelial cells are preferably washed with acid pH values and binding studies with paf, LA-paf, analogues of paf, paf antagonists and antibodies are performed as described above and according to step c) the differentiated and non-differentiated endothelial cells are compared in the absence and presence of labelled and unlabelled agonists and antagonists, d) genes producing endothelial paf receptors according to c) are defined. Endothelial cells are cultured and differentiated to transfer genes encoding very high affinity paf receptors into soluble cells for example cancer cells or bacterial cells using standard procedures. Endothelial cells are cultured on soluble particles. Next, soluble cells and soluble particles with endothelial cells producing paf receptors are used to test substances for example specifically related against high, very high or moderate affinity paf receptors using screening procedures for example with automatons.

The culture of endothelial cells or endothelial cell lines for example Im-Huvec can be performed for example with all standard culture techniques described. The endothelial cells for example immortalized endothelial cells can be cultured also on soluble particles to further facilitate the procedure. The culture dishes and soluble particles can also be mixed for example with gelatine and growth factors, hormones, mediators, lipids and antagonists. Endothelial cells can also be grown on smooth muscle cells to define and treat cellular interactions leading to vascular regulation. In this context, functional assays can be used for example calcium influx or production and release of mediators in the absence and presence of antagonists and antibodies.

To test the expression of paf receptors for example in response to insulin binding studies according to c) are performed for example after culture in the presence of for example 2 I.E. human insulin with its addition to a standard medium for preferably 2 to 24 hr. Other growth factors and compounds can be added. Compounds including pharmacological compounds antagonizing the production and expression of paf receptors and/or the receptors themselves can be added. According to the invention binding studies are performed with unlabelled and/or labelled lipids for example colored, radioactive, fluorescence paf, LA-paf, agonists and antagonists and antibodies as well as lipoproteins.

EXAMPLE 2: CELLULAR LA-PAF PRODUCTION 2.1 Endothelial cells:

Endothelial cells metabolized exogenously added [$^3$H]paf to labelled LA-paf (FIG. 2). Extraction as well as phospholipid purification with HPLC was performed as described [R. Korth, Brit. J. Pharmacol. 98, 653–661]. The LA-paf peak was exclusively found in endothelial cells whereas lyso paf was found in endothelial supernatants. Addition of unlabelled paf decreased the peak showing endothelial paf metabolism (to LA-paf) is a receptor-dependent phenomenon. According to the invention antagonists against very high affinity paf receptors are in parallel antagonists against LA-paf production. In addition, antagonist inhibits the LA-paf interaction with very high affinity receptors by preference on endothelial cells. In contrast, LA-paf interaction with high affinity paf receptors on washed human platelets was distinct because platelets did not metabolize added paf [R. Korth, Brit. J. Pharmacol. 98, 653–661]. According to the invention, endothelial cells metabolized exogenously added labelled paf (0.3 or 0.65 nM) to labelled LA-paf as 26 and 17 percent or 16 and 11 percent of added label eluted with 9–15 min from standard HPLC comigrating with LA-paf. However, LA-paf comigrates in standard HPLC also with biologically inactive long-chain paf metabolites.

2.1. Use of soluble cells:

According to the invention soluble cells are used to produce LA-paf as the number of freshly prepared endothelial cells is limited. LA-paf is produced in vitro by incubation of soluble cells in the presence of serum. According to the invention soluble cells for example cancer cell lines or bacterial cells are suitable. Soluble cells are for example a human histiocyte lymphoma cell line with monocyte/macrophage like qualities such as U 937 cells (ATCC 6th Edition CRL 1593, p.154).

According to the invention cells are incubated for example 48 hr in 10% foetal calf serum using standard procedure. The biologically active LA-paf is purified with standard phospholipid extraction and HPLC to be quantified using aggregation of rabbit platelets washed as described before using human platelets [R. Korth, European Patent Application (1990) Bulletin 91/49, Publication Number 0 459 432 A1].

According to the invention soluble cells metabolize exogenously added [$^3$H]paf to labelled LA-paf. Resident U 937 cells carry huge amounts of biologically active LA-paf (41 ng LA-PAF per 10$^7$ cells). Labelled LA-paf is produced as radioactivity eluted together with biologically active LA-paf from standard phase HPLC after 9–15 min (Table I). [$^3$H]paf remained intact in the control buffer (1 h at 37° C.) excluding [$^3$H]paf degradation.

TABLE I: Production of labelled LA-paf during cellular metabolism of [$^3$H]paf

The [$^3$H]paf metabolism of soluble cells by preference of monocyte/macrophage like U 937 lymphoma cells was investigated. [$^3$H]paf (2.5 nM) was added for 1 hr incubation period at 37° C. to washed soluble cells (2.5×10$^6$ per ml) before phospholipid analysis was performed with standard HPLC. Values are expressed as percentage of the total label (166 931 dpm) after subtraction of the background values.

| Retention time: | void volume | 9–15 min LA-Paf | 18–21 min paf | 28–31 min lyso paf |
|---|---|---|---|---|
| Percentage: | | % | % | % |
| Experiment 1: | 1.8 | 20 | 78 | 0.2 |
| Experiment 2: | 4.5 | 32 | 61 | 2.9 |

Footnotes:

Abbreviations used: Lipoprotein-associated platelet activating factor (LA-paf). Low density lipoproteins (LDL), very low density lipoproteins (VLDL) and high density lipoproteins (HDL). Inhibitory fifty percent values (IC$_{50}$). Fatty acid free bovine serum albumin (BSA), acid citrate dextrose (ACD), foetal calf serum (FCS), phorbol-12-myristate-13-acetate (PMA).

Materials:

Cells were washed in Tyrode's buffer and materials were used as described [R. Korth et al. (1988) Eur. J. Pharmacol. 152, 101–110; R. Korth et al. (1989) Brit. J. Pharmacol. 98, 653–661]. BSA (fraction V) and PMA were from Sigma (St. Louis, Mo., U.S.A.). Radiolabelled synthetic paf in the position 1 of the molecule ([$^3$H]paf, 80 Ci/mmol) as well as PCS and OCS scintillation fluid were from Amersham (Amersham, U.K.) and were dissolved in pure ethanol. Unlabelled synthetic paf was from Bachem, (Bubendorf, Switzerland) and solubilized in ethanol. Human Insulin was from Hoechst (Germany). Immortalized human umbilical vein endothelial cells (Im-Huvec) were obtained from Patrick Vicard and Denise Paulin (Institute Pasteur, France). The human histiocytic lymphoma cell line U 937 was established 1974 by C. Sundstrom and K. Nilsson [Int. J. Cancer 17 (1976), 565–577]. They were obtained from American Type Culture Collection (AtCC 6th Ed. CRL 1593).

Discussion

The invention refers to simple and quick methods to test the efficacy of LA-paf antagonists and antagonists against very high affinity paf receptors on endothelial cells. According to the invention endothelial cells for example immortalized cells produced very high affinity paf receptors during their differentiation. According to the invention it is suitable to transfer either endothelial genes after differentiation on soluble cells or culture endothelial cells on soluble particles to test antagonists for example by automatons. The invention refers also to a simple procedure of in vitro production of labelled LA-paf for example in endothelium cells. According to the invention it is suitable to use soluble cells for a screening procedure to test antagonists against very high affinity paf receptors with related LA-paf production.

The procedure is suitable for the production of active ingredients in conventional pharmaceutical preparations and paf antagonists can be used for prevention and treatment of pathological irritation, differentiation, aging or death of cells in vitro and in vivo. According to the invention cell differentiation for example in response to insulin correlates with the production of endothelium receptors. According to the invention non-differentiated cells differentiate in response to various (non-specific) factors for example with protein kinase C activators such as PMA, atherogenetic factors such as LDL, steroids such as cholesterol, growth factors such as insulin, various proteins such as cytokines and acid pH values to produce paf receptors.

According to the invention different cells produce distinct paf receptors during cell differentiation. According to the invention the specific antagonist to be tested prevent or antagonize paf receptors also in vivo. Thus, paf antagonists can be administered to an individual with pathological differentiation by preference of endothelial cells. The treatment of pathological cell differentiation for example during hyperlipidemia, hyperinsulinemia and acid pH-values prevents or treats growing old before age. The differentiation factors are not cell-specific for example lipoproteins such as LDL, steroids such as cholesterol, cancer factors such as PMA or growth factors such as insulin or various proteins such as cytokines can be used. These compounds are all risk factors for the development of vascular diseases, accelerated aging with or without mental syndroms.

For screening procedures in vitro for example with automatons it is suitable to use soluble cells by preference after gene transfer or soluble particles with adherent cells. According to the invention for example adherent immortalized endothelial cells could be cultivated on soluble particles for a screening procedure. According to the invention two cell lines produce distinct paf receptors, for example differentiated monocyte/macrophage like cells produced high affinity (ha) paf receptors [R. Korth, U.S. patent application Ser. No. 07/845,088] and endothelial cells as well as differentiated immortalized endothelial cells produce very high affinity (vha) paf receptors. According to the invention antibodies can also be produced because genes mediating the formation of endothelial cells can be enriched and a gene transfer from endothelial cell lines to soluble cells can be performed. The difference between differentiated vs. non-differentiated cells with presence and absence of paf receptors can be used to produce antibodies using standard procedures. Antibodies against surface proteins of non-differentiated cells are subtracted from those on differentiated cells using screening procedures according to the invention.

Thus, the invention is suitable to determine specific antagonists (and antibodies) for example against distinct paf receptors in vitro using screening procedures for example with automatons. The efficacy of paf antagonists can also be tested with radio- and fluorescence labelled or colored compounds for example antibodies with agonist and antagonist potency. According to the invention endothelial cells for example immortalized human umbilical vein endothelial cells are preferably stimulated as resident non-differentiated cells had a lower number of paf receptors. According to the invention a non-specific long time stimulation of non-differentiated cells is suitable either by infection, atherogenetic lipoproteins, steroids such as cholesterol or growth factors such as insulin. According to the invention cells can be also stimulated for a shorter incubation period by acid treatment or activation of the protein kinase C for example with PMA or acid pH values.

An irritation of the protein kinase C for example by the tumor promoting factor PMA has a considerable importance in cancer. According to the invention PMA expressed paf receptors on human lymphoma U 937 cells. According to the invention the expression of paf receptors on cancer cells interfered with cell differentiation (aging) and protein kinase C activation. It is now suitable to find compounds which prevent or treat cancer disease or metastasis. Quite surprisingly, also infected non-differentiated cancer cells expressed paf receptors for example on the surface of monocyte/macrophage like U 937 cells after mycoplasma infection (our unpublished data).

According to the invention endothelial cells metabolized exogenously added [$^3$H]paf to LA-paf and cells carried biological active LA-paf. LA-paf was obviously not recognized by the cellular acetylhydrolase as LA-paf accumulated in cells for example soluble lymphoma cells. Thus, the invention refers to a simple and quick production of LA-paf by preference of soluble cell lines for example cancer cells or bacterial cells.

According to the invention, LA-paf is produced during oxidation of long chain fatty acid derivates for example of the cellular paf metabolite alkyl-acyl-glyceryl-phosphoryl-choline. Thus, LA-paf antagonists inhibit either the receptor-dependent interaction of lipids such as paf or LA-paf or the cellular oxidation of long chain fatty acid derivates by preference with or without antioxidant substances. By preference lipoproteins differentiate cells but they also interact with paf receptors and are LA-paf carriers from inside the vessels out for example via cell emigration or via receptor-dependent lipoprotein transport through the endothelium monolayer. According to the invention, antagonists inhibit perivascular degeneration. The invention refers to a simple procedure to produce LA-paf for example by incubation of soluble lymphoma cells with serum.

In addition, the invention facilitate to administer natural ginkgolides for example with food. Thus, the invention helps to compose "FIDA infants' foods for invalids and seniors" [R. Korth U.S. Trademark application, Ser. No. 74/416579, date of filing Jul. 26, 1993]. Then, "FIDA-infants' foods for invalids and seniors" antagonize disorders caused by infection, irritation, differentiation, aging or cell death. Antagonists can also be administered as beauty products because they prevent and treat irritation, pathological differentiation, aging and death of cells for example endothelial cells with degeneration of the perivascular tissue. In the latter case the increased number of fibroblasts, emigrated blood cells or smooth muscle cells are prevented. According to the invention, LA-paf is present in resident healthy cells when paf is completely absent.

These findings are relevant to conduct quick and simple procedures to find specific antagonists against high and very high affinity paf receptors via screening procedures. These antagonists prevent or treat pathological irritation, differentiation, aging or death of cells in vitro and in vivo. The invention refers also to an in vitro production of labelled and unlabelled LA-paf using soluble cells to further facilitate the screening procedure to test LA-paf antagonists.

I claim:

1. A method of treatment or prevention of irritation of endothelial cells, in a subject who either has or is at risk of developing a condition selected from the group consisting of hyperlipidemia, acid pH blood value, and hyperinsulinemia, said method comprising administering an effective amount of an antagonist against LA-paf to said subject wherein the antagonists is a chemically defined ginkgolide mixture and the chemically defined ginkgolide mixture is directed against very high affinity receptors on endothelial cells to prevent and inhibit the binding or production of LA-paf.

2. The method according to claim 1 wherein the antagonists are administered with food.

3. The method according to claim 2 wherein the antagonist is the chemically defined ginkgolide mixture BN 52063.

4. The method according to claim 3 wherein BN 52063 is a mixture of 9H-1, 7a-(Epoxymethano)-1H, 6aH-cyclopenta(c)furo( 2,3-b) furo(3',2':3,4) cyclopenta (1,2-d) furan-5, 9,12 (4H)-trione, 3-tert-butylhexahydro-4,7b-dihydroxy-8-methyl; 9H-1, 7a-(Epoxymethano)-1H,6aH-cyclopenta(c)furo(2,3-b)furo-( 3',2':3,4) cyclopenta(1,2-d) furan-5,9,12(4H)-trione, 3 tert-butylhexahydro-4, 4b-11-trihydroxy-8-methyl and 9H-1, 7 a-(Epoxymethano)-1H, 6aH-cyclopenta(c)furo(3',2':3,4) cyclopenta (1,2-d) furan-5,9,12 (4H) -trione, 3 tert-butyl hexahydro-2,4,7b, 11 -tetrahydroxy-8-methyl.

5. The method according to claim 1 wherein the antagonists are administered topically.

6. The method according to claim 5 wherein the antagonists is the chemically defined ginkgolide mixture BN 52063.

7. The method according to claim 6 wherein BN 52063 is a mixture of 9H-1, 7a-(Epoxymethano)-1H, 6aH-cyclopenta(c)furo( 2,3-b)furo(3',2':3,4) cyclopenta (1,2-d) furan-5,9, 12 (4H)-trione, 3-tert-butylhexahydro-4, 7b-dihydroxy-8-methyl; 9H-1, 7a-(Epoxymethano)-1H,6aH-cyclopenta(c)furo(2,3-b)furo-( 3',2':3,4) cyclopenta(1,2-d) furan-5,9,12(4H)-trione, 3 tert-butylhexahydro-4, 4b-11-trihydroxy-8-methyl and 9H-1, 7 a-(Epoxymethano)-1H, 6aH-cyclopenta(c)furo(3',2':3,4) cyclopenta (1,2-d) furan-5,9,12 (4H)-trione, 3 tert-butyl hexahydro-2,4,7b,11 -tetrahydroxy-8-methyl.

* * * * *

UNITED STATES PATENT AND TRADEMARK OFFICE
CERTIFICATE OF CORRECTION

PATENT NO. : 5,530,023

DATED : June 25, 1996

INVENTOR(S) : Korth

It is certified that error appears in the above-identified patent and that said Letters Patent is hereby corrected as shown below:

Title page

Item [76], delete " 9, D-806390 " and insert therefor -- 7A, D-80639 --.

Title page

Item [30], please insert --

| | | |
|---|---|---|
| October 20, 1987 | [DE] Germany | P 37 35 525.2 |
| June 6, 1990 | [DE] Germany | P 40 17 818.8 |
| October 20, 1990 | [DE] Germany | P 40 34 090.2 -- |

Figure 1B:
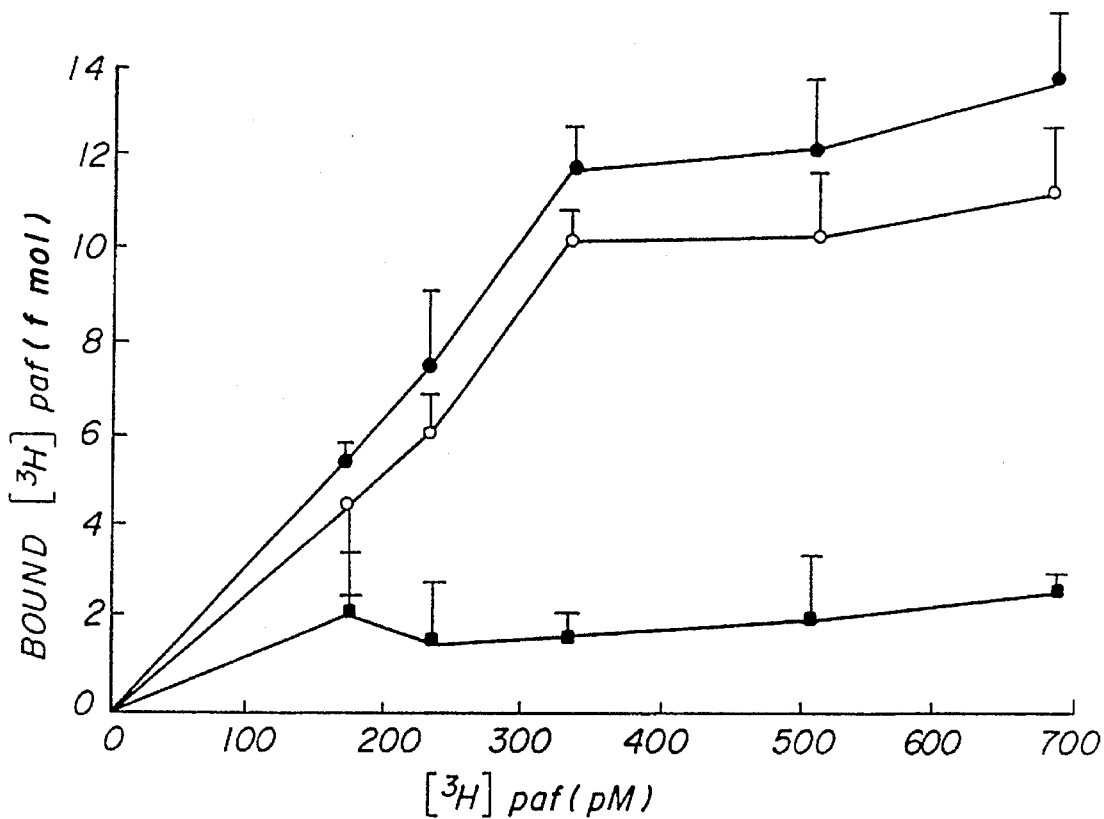
FIG. 1B

Column 6, line 45, delete " FIG. 1A " and insert therefor -- FIG. 1A and 1B --

Figure 2A:
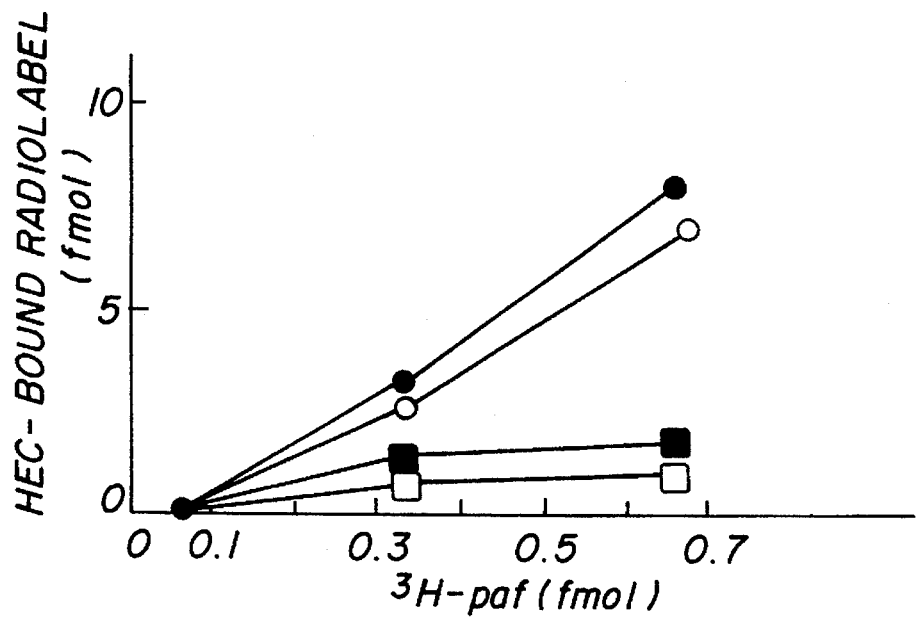
Figure 2B:
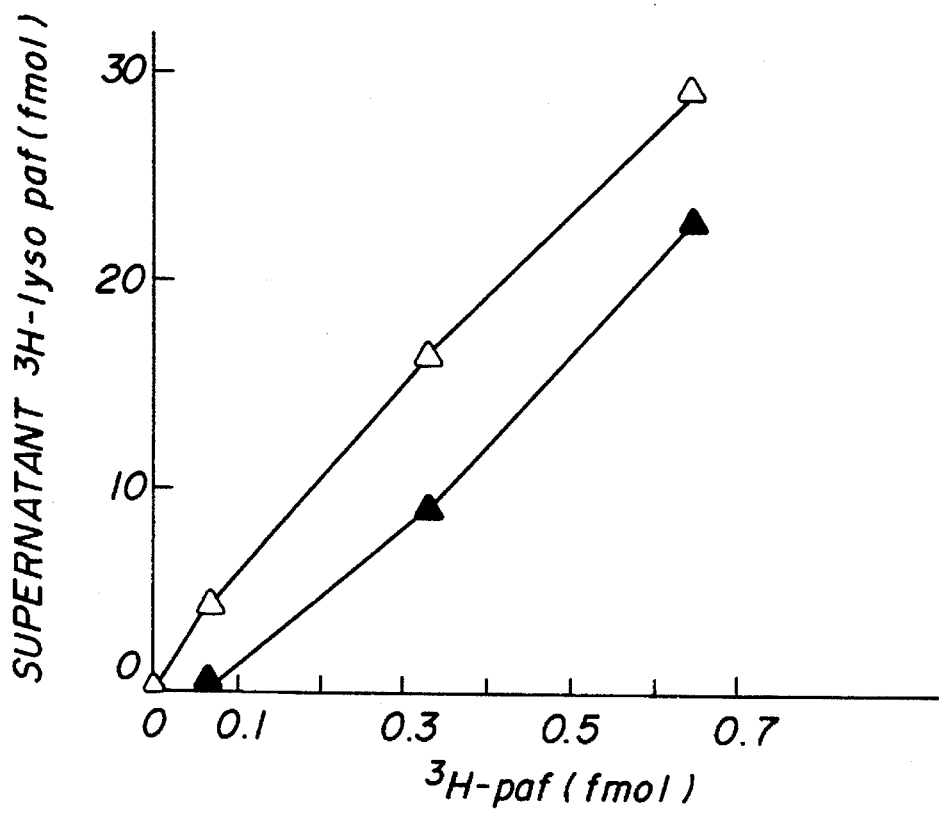

Column 6, line 60, delete " FIG. 2A " and insert therefor -- FIG. 2A and 2B --

Column 7, line 31, delete "))" and insert therefor -- ) --.

Claim 4, line 23; and Claim 4,(Column 14) line 4, delete " furo(3',2':3,4) " and insert therefor -- furo-[3',2':3,4] --.

Claim 7, lines 15 and 21, delete " furo(3',2':3,4) " and insert therefor -- furo-[3',2':3,4] --.

UNITED STATES PATENT AND TRADEMARK OFFICE
CERTIFICATE OF CORRECTION

PATENT NO. : 5,530,023
DATED : June 25, 1996
INVENTOR(S) : Korth

It is certified that error appears in the above-identified patent and that said Letters Patent is hereby corrected as shown below:

Column 3, line 43, delete " 4b " and insert therefor -- 4, 7b-11- --.

Claim 4, line 2, delete " 4b " and insert therefor -- 4, 7b-11- --. (Column 14)

Claim 7, line 19, delete " 4b " and insert therefor -- 4, 7b-11- --.

Column 3, line 45, delete " (c) " and insert therefor -- [c]furo [2,3-b] --.

Claim 4, line 4, delete " (c) " and insert therefor -- [c]furo [2,3-b] --. (Column 14)

Claim 7, line 21, delete " (c) " and insert therefor -- [c]furo [2,3-b] --.

Column 3, lines 38 and 41, delete " 7a-Epoxymethano) " and insert therefor -- 7a-(Epoxymethano) --.

Column 3, lines 43 and 46, delete " 3 tert- " and insert therefor -- 3-tert- --.

Claim 4, lines 2 and 5, delete " 3 tert- " and insert therefor -- 3-tert- --. (Column 14)

Claim 7, lines 19 and 22, delete " 3 tert- " and insert therefor -- 3-tert- --.

Column 3, lines 38 and 39, Column 3, line 42, Column 3, lines 45 and 46, please delete " penta(c)furo(3',2':3,4)cyclopenta(1,2-d) " and insert therefor -- penta[c]furo[2,3-b]furo-[3',2':3,4]cyclopenta[1,2-d] --.

UNITED STATES PATENT AND TRADEMARK OFFICE
CERTIFICATE OF CORRECTION

PATENT NO. : 5,530,023
DATED : June 25, 1996
INVENTOR(S) : Korth

It is certified that error appears in the above-identified patent and that said Letters Patent is hereby corrected as shown below:

Claim 4, Column 13, line 23; Column 14, lines 1 and 4, please delete "penta(c)furo(3',2':3,4)cyclopenta(1,2-d) " and insert therefor -- penta[c]furo[2,3-b]furo-[3',2':3,4]cyclopenta[1,2-d] --.

Claim 7, lines 15, 18 and 21, please delete "penta(c)furo(3',2':3:4)cyclopenta(1,2-d) " and insert therefor -- penta[c]furo[2,3-b]furo-[3',2':3,4]cyclopenta[1,2-d] --.

Signed and Sealed this

Sixth Day of January, 1998

Attest:

BRUCE LEHMAN

*Attesting Officer*  *Commissioner of Patents and Trademarks*